US009435741B2

(12) United States Patent
Kobayashi et al.

(10) Patent No.: US 9,435,741 B2
(45) Date of Patent: Sep. 6, 2016

(54) SPECTROMETRY DEVICE AND SPECTROMETRY METHOD

(75) Inventors: Minoru Kobayashi, Osaka (JP); Taisuke Ota, Osaka (JP)

(73) Assignee: Nanophoton Corporation, Osaka (JP)

( * ) Notice: Subject to any disclaimer, the term of this patent is extended or adjusted under 35 U.S.C. 154(b) by 203 days.

(21) Appl. No.: 13/819,309

(22) PCT Filed: Aug. 30, 2011

(86) PCT No.: PCT/JP2011/004816
§ 371 (c)(1), (2), (4) Date: Feb. 26, 2013

(87) PCT Pub. No.: WO2012/029286
PCT Pub. Date: Mar. 8, 2012

(65) Prior Publication Data
US 2013/0162990 A1 Jun. 27, 2013

(30) Foreign Application Priority Data
Aug. 30, 2010 (JP) ................................ 2010-191946

(51) Int. Cl.
*G01J 3/44* (2006.01)
*G01N 21/65* (2006.01)
*G01J 3/02* (2006.01)
*G01J 3/457* (2006.01)

(52) U.S. Cl.
CPC ............... *G01N 21/65* (2013.01); *G01J 3/021* (2013.01); *G01J 3/44* (2013.01); *G01J 3/457* (2013.01)

(58) Field of Classification Search
CPC ............ G01J 3/44; G01J 3/457; G01J 3/021; G01N 21/65
USPC ........................................................ 359/381
See application file for complete search history.

(56) References Cited

U.S. PATENT DOCUMENTS 5,455,673 A 10/1995 Alsmeyer et al.
5,638,172 A 6/1997 Alsmeyer et al.
5,652,853 A 7/1997 Alsmeyer et al.
5,712,167 A 1/1998 Yamaguchi et al.
6,175,750 B1 1/2001 Cook et al.
2006/0055919 A1* 3/2006 Lee .......................... G01J 3/44 356/301

(Continued)

FOREIGN PATENT DOCUMENTS

JP 09-089896 4/1997
JP 10-038807 2/1998

(Continued)

*Primary Examiner* — Kara E Geisel
*Assistant Examiner* — Dominic J Bologna
(74) *Attorney, Agent, or Firm* — Fanelli Haag PLLC

(57) ABSTRACT

A spectrometry device according to an aspect of the present invention is including a light source (101), a lens 104 concentrating a light beam from the light source (101) on a reference sample (120), an objective lens (106) concentrating a light beam that has passed through the first lens (104) on a measurement sample (121), a spectroscope (109) dispersing light having a different wavelength from that of the light beam generated in the measurement sample (121) and the reference sample (120) by irradiation of the light beam into a spectrum, a detector (110) detecting light that is dispersed by the spectroscope (109), and a beam splitter (103) separating an optical path of light from the reference sample (120) and the measurement sample (121) toward the spectroscope (109) from an optical path of a light beam that propagates from the light source (101) toward the measurement sample (121).

15 Claims, 9 Drawing Sheets

101 102 103 104 105 106
120 121
107
108
110
109
100

(56) References Cited

U.S. PATENT DOCUMENTS

| | | | | |
|---|---|---|---|---|
| 2007/0132994 | A1* | 6/2007 | Kobayashi et al. | 356/328 |
| 2007/0145258 | A1* | 6/2007 | Nelson et al. | 250/252.1 |
| 2008/0316478 | A1* | 12/2008 | Slawinski et al. | 356/300 |

FOREIGN PATENT DOCUMENTS

| | | |
|---|---|---|
| JP | 10-501333 | 2/1998 |
| JP | 2001-066197 | 3/2001 |
| JP | 2002-540391 | 11/2002 |
| JP | 2003-524744 | 8/2003 |
| JP | 2005-114539 | 4/2005 |
| JP | 2007-179002 | 7/2007 |
| WO | WO 95/33189 | 12/1995 |
| WO | WO 00/57146 | 9/2000 |
| WO | WO 01/14860 | 3/2001 |

* cited by examiner 121
106
105
120
104
131
132
103
107
108
109
102
110
101
111
100

SPECTRUM AT A

SPECTRUM AT B

SPECTROMETRY DEVICE AND SPECTROMETRY METHOD

This application is a U.S. National Stage Application of PCT International Patent Application No. PCT/JP2011/004816, which was filed on Aug. 30, 2011 and claims priority to Japanese Patent Application No. 2010-191946, which was filed Aug. 30, 2010, the disclosure of each of which is incorporated herein by reference in its entirety.

TECHNICAL FIELD

The present invention relates to a spectrometry device and a spectrometry method, in particular a spectrometry device and a spectrometry method in which light from a reference sample and a measurement sample is dispersed and measured.

BACKGROUND ART

In recent years, Raman spectrometry devices, in which spectrometry is performed for Raman scattered light, have been widely used (Patent literature 1). For example, in the evaluation of a manufacturing process for semiconductor devices such as Si, a stress is measured by using a Raman microscope. The stress is obtained based on the peak position(s) of a Raman spectrum. To obtain a stress in the order of 100 MPa, it is necessary to determine the peak position with relatively high accuracy, e.g., accuracy in the order of 0.1 $cm^{-1}$. In order to determine the peak position without being affected by fluctuations in the room temperature and the like, a method using an argon laser plasma line as a reference light is disclosed (Patent literature 2).

The configuration of Patent literature 2 is explained with reference to FIG. 8, Laser light emitted from a laser light source 201 is expanded by a beam expander 202. Then, the laser light passes through a half mirror 203 and enters an objective lens 204. The objective lens 204 concentrates the laser light on a measurement sample 221. Then, Raman scattered light generated on the measurement sample 221 is incident on the half mirror 203 through the objective lens 204. The half mirror 203 reflects the Raman scattered light toward a lens 205. The lens 205 concentrates the Raman scattered light onto a slit 206 of a spectroscope 207. Then, the Raman scattered light, which has passed through the slit 206, is dispersed by the spectroscope 207 and detected by a CCD detector 208, in this way, it is possible to measure a Raman spectrum. Then, the temperature is obtained based on the peak position of the Raman spectrum.

However, in this method, it is necessary to use a relatively large argon laser, and thus causing a problem that downsizing of the apparatus is very difficult. As another method, a method for obtaining reference light by splitting laser light is disclosed (Patent literature 3). In this method, the peak position is obtained by using a reference light. Further, the method uses shutters that are used to block the exciting light and the reference light respectively.

CITATION LIST

Patent Literature

Patent literature 1: Japanese Unexamined Patent Application Publication No. 2007-179002

Patent literature 2 Japanese Unexamined Patent Application Publication No. 2001-66197

Patent literature 3: Japanese Unexamined Patent Application Publication No. 2005-114539

SUMMARY OF INVENTION

Technical Problem

In Patent literature 3, the optical path for the reference light and the optical path for the exciting light are split by using a half mirror. A configuration for splitting the reference light by using a half mirror and thereby for illuminating a reference sample is explained hereinafter with reference to FIG. 9. In the configuration shown in FIG. 9, a half mirror 209 and a lens 210 are further provided in the optical configuration shown in FIG. 8. The exciting light, which is split at the half mirror 209, is incident on a reference sample 220 through the lens 210. Then, Raman scattered light generated on the reference sample 220 is incident on the half mirror 209 through the lens 210. The half mirror 209 combines the Raman scattered light generated in the reference sample 220 with Raman scattered light generated in the measurement sample 221. Then, the combined Raman scattered light enters a slit 206 disposed on the incident side of a spectroscope 207 through a half mirror 203 and a lens 205. In this manner, Raman spectrometry is carried out.

However, there are following problems in this method: (1) the manufacturing cost of the apparatus increases because the method requires a new optical system for the reference sample; and (2) losses of the laser light and the Raman scattered light occur, when the measurement sample and the reference sample are simultaneously measured, because the beam is split. Further, in the optical system using line illumination as shown in Patent literature 1, there is such a problem that (3) since the incident angle to the split mirror is not fixed, it is very difficult to align the exciting light intensity distribution and the detection sensitivity distribution along the line in the measurement sample and the reference sample.

Therefore, in conventional Raman spectrometry devices, there is a problem that when peak positions of a reference sample and a measurement sample are measured, the optical system becomes complicated, and thus increasing the cost. Further, the above-described problems are not limited to the Raman spectrometry but also occur in other secondary lights such as fluorescence.

The present invention has been made in view of the above-described problems and an object thereof is to provide a spectrometry device and a spectrometry method capable of performing highly accurate measurement with ease.

Solution to Problem

A spectrometry device according to a first aspect of the present invention is a spectrometry device that performs spectrometry for light generated in a measurement sample and a reference sample and thereby detects respective peak positions in spectrums of the measurement sample and the reference sample, including: a light source; a first lens that concentrates a light beam from the light source on the reference sample; a second lens that concentrates a light beam that has passed through the first lens on the measurement sample; a spectroscope that disperses light that is generated in the measurement sample and the reference sample by irradiation of the light beam and has a different wavelength from that of the light beam into a spectrum; a detector that detects light that is dispersed by the spectroscope; and light splitting means for separating an optical path of light that is heading from the reference sample and the measurement sample toward the spectroscope from an optical path of a light beam that is heading from the light source toward the measurement sample. As a result, it is possible to carry out highly accurate measurement with a simple configuration.

A spectrometry device according to a second aspect of the present invention is the above-described spectrometry device, further including a processing device that refers to known spectrum information of the reference sample and thereby distinguishes between a peak position in a spectrum of the reference sample and a peak position in a spectrum of the measurement sample. As a result, it is possible to carry out measurement with high accuracy.

A spectrometry device according to a third aspect of the present invention is the above-described spectrometry device, in which the reference sample is disposed on an optical axis of the first lens, and a light beam from the light source passes through the reference sample and then is incident on the measurement sample through the second lens. As a result it is possible to simultaneously irradiate the reference sample and the measurement sample and thereby to simplify the configuration.

A spectrometry device according to a fourth aspect of the present invention is the above-described spectrometry device, further including scan means for deflecting the light beam and thereby scanning a position of a light beam on the measurement sample, in which the reference sample is disposed out of an optical axis of the first lens, and the scan means deflects the light beam and thereby makes the light beam that is originally incident on the measurement sample incident on the reference sample. As a result, it is possible to use various reference samples.

A spectrometry device according to a fifth aspect of the present invention is the above-described spectrometry device, in which the reference sample is movably disposed so that a distance from the reference sample to the first lens can be changed. As a result, it is possible to adjust the intensity of the reference light from the reference sample.

A spectrometry device according to a sixth aspect of the present invention is the above-described spectrometry device, in which light that is heading from the reference sample and the measurement sample toward the spectroscope is incident on a plurality of pixels of the detector, arranged along an entrance slit disposed on an incident side of the spectroscope, and spectrums of the measurement sample and the reference sample are measured by changing a wavelength range that is dispersed over a row of pixels of the detector by the spectroscope. As a result, it is possible to align the light intensity distribution and the detection sensitivity distribution with ease.

A spectrometry device according to a seventh aspect of the present invention is the above-described spectrometry device, in which a peak position in the measurement spectrum is measured by using at least two peak positions contained in spectrum information of the reference sample. As a result, it is possible to improve the measurement accuracy.

A spectrometry device according to an eighth aspect of the present invention is the above-described spectrometry device, in which light that is heading from the reference sample and the measurement sample toward the spectroscope is incident on a plurality of pixels of the detector, arranged along an entrance slit disposed on an incident side of the spectroscope, and a peak position in a spectrum is detected at each of at least two places along a direction of the entrance slit. As a result, it is possible to carry out highly accurate measurement at high speed.

A spectrometry method according to a ninth aspect of the present invention is a spectrometry device for performing spectrometry for light generated in a measurement sample and a reference sample and thereby detecting respective peak positions in spectrums of the measurement sample and the reference sample, including: a step of concentrating a light beam from a light source on the reference sample by a first lens; a step of concentrating a light beam that has passed through the first lens on the measurement sample by a second lens; a step of separating light that is generated in the measurement sample and the reference sample by irradiation of the light beam and has a different wavelength from that of the light beam from light that is heading from the light source toward the measurement sample; and a step of dispersing light that is generated in the measurement sample and the reference sample and has a different wavelength from that of the light beam into a spectrum. As a result, it is possible to carry out highly accurate measurement with a simple configuration.

A spectrometry device according to a tenth aspect of the present invention is the above-described spectrometry device, in which a peak position in a spectrum of light from the reference sample and a peak position in a spectrum of the measurement sample are distinguished by referring to spectrum information of light from the reference spectrum. As a result, it is possible to carry out measurement with high accuracy.

A spectrometry method according to an eleventh aspect of the present invention is the above-described spectrometry method, in which the reference sample is disposed on an optical axis of the first lens, and a light beam from the light source passes through the reference sample and then is incident on the measurement sample through the second lens. As a result, it is possible to simultaneously irradiate the reference sample and the measurement sample and thereby to simplify the configuration.

A spectrometry method according to a twelfth aspect of the present invention is the above-described spectrometry method, further including a step of deflecting the light beam and thereby scanning a position of a light beam on the measurement sample, in which the reference sample is disposed out of an optical axis of the first lens, and the scan means deflects the light beam and thereby makes a light beam that originally is incident on the measurement sample incident on the reference sample. As a result, it is possible to use various reference samples.

A spectrometry method according to a thirteenth aspect of the present invention is the above-described spectrometry method, which the reference sample is movably disposed so that a distance from the reference sample to the first lens can be changed. As a result, it is possible to adjust the intensity of the reference light from the reference sample.

A spectrometry method according to a fourteenth aspect of the present invention is the above-described spectrometry method, in which a light beam from the light source is concentrated into a line-like spot and then is incident on the measurement sample and the reference sample, and spectrums of the measurement sample and the reference sample are measured by changing a wavelength range that is dispersed over a row of pixels of the detector by the spectroscope. As a result, it is possible to align the light intensity distribution and the detection sensitivity distribution with ease.

A spectrometry method according to a fifteenth aspect of the present invention is the above-described spectrometry method, in which a peak position in the measurement spectrum is measured by using at least two peak positions contained in known spectrum information of the reference sample. As a result, it is possible to carry out measurement with higher accuracy.

A spectrometry method according to a sixteenth aspect of the present invention is the above-described spectrometry method, in which light that is heading from the reference sample and the measurement sample toward the spectroscope is incident on a plurality of pixels of the detector, arranged along an entrance slit disposed on an incident side of the spectroscope, and a peak position in a spectrum is detected at each of at least two places along a direction of the entrance slit. As a result, it is possible to carry out highly accurate measurement at high speed.

Advantageous Effects of Invention

According to the present invention, it is possible to provide a spectrometry device and a spectrometry method capable of performing highly accurate measurement with ease.

DESCRIPTION OF EMBODIMENTS

First Exemplary Embodiment

Figure 1:
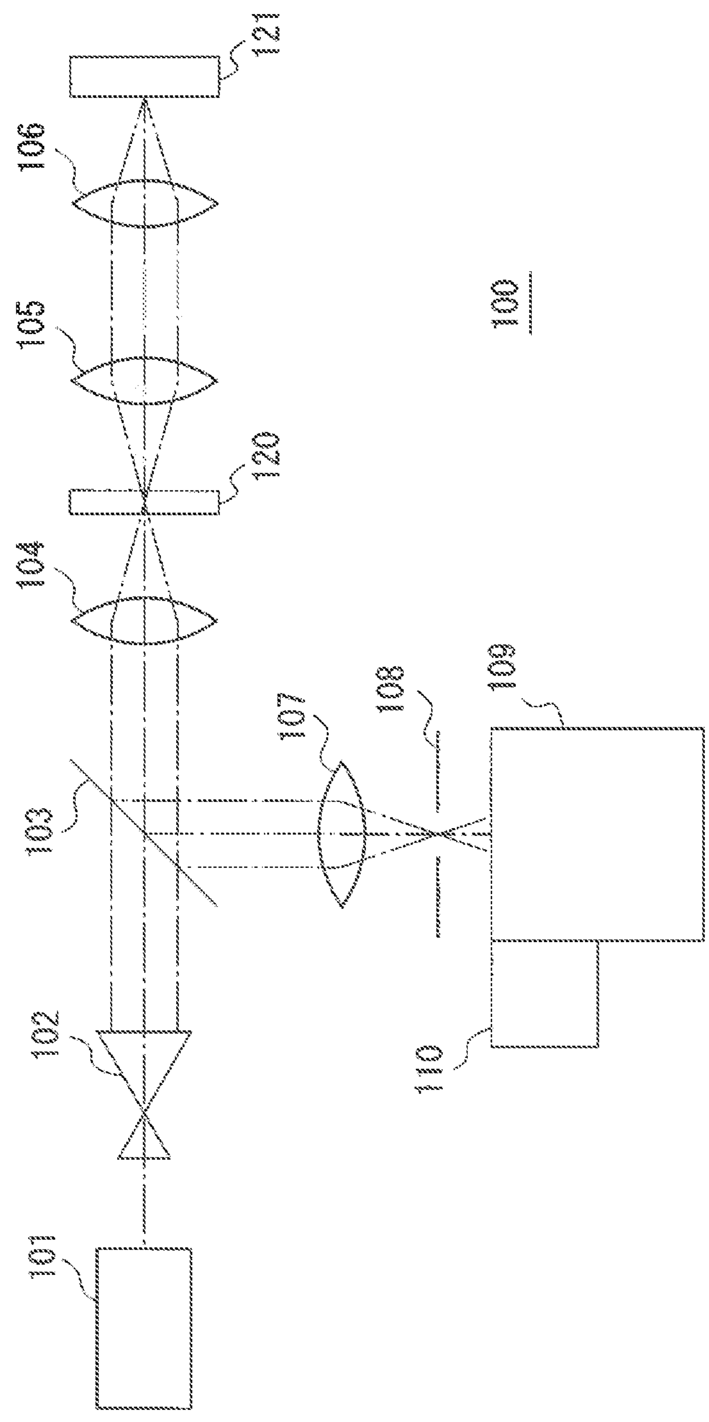
FIG. 1 shows a configuration of a spectrometry device according to a first exemplary embodiment.

Exemplary embodiments according to the present invention are explained hereinafter with reference to the drawings. Firstly, an overall configuration of a spectrometry device according to this exemplary embodiment is explained with reference to FIG. 1, FIG. 1 shows a spectrometry device. A spectrometry device according to this exemplary embodiment is a Raman spectrometry device that disperses Raman scattered light generated in a sample and thereby measures the Raman scattered light.

As shown in FIG. 1, a spectrometry device 100 includes a laser light source 101, a beam expander 102, a beam splitter 103, a lens 104, a lens 105, an objective lens 106, a lens 107, an entrance slit 108, a spectroscope 109, and a detector 110. The spectrometry device 100 is a Raman microscope that detects Raman scattered light, and includes the spectroscope 109 for performing spectrometry. Further, Raman spectrometry is performed by simultaneously irradiating a reference sample 120 and a measurement sample 121 with laser light.

The laser light source 101 emits monochromatic laser light. The laser light source 101 emits laser light having a predetermined laser wavelength. This laser light serves as exciting light for exciting the measurement sample 121 and the reference sample 120. Needless to say, there are no particular restrictions on the light source used as the light source for exciting light. In this exemplary embodiment, there is no need to use a large laser light source such as an argon laser. Therefore, it is possible to use a compact laser light source and thereby to reduce the apparatus in size.

The light beam from the laser light source 101 is expanded by the beam expander 102. The laser light, whose spot has been expanded by the beam expander 102, becomes collimated light. Then, the laser light from the beam expander 102 is incident on beam splitter 103. The beam splitter 103 is, for example, a dichroic mirror, and lets light having the laser wavelength pass therethrough toward the measurement sample 121. Note that light splitting means other than the dichroic mirror can be also used as the beam splitter 103. For example, a polarized light beam splitter or a half mirror can be used as the light splitting means.

The laser light that has passed through the beam splitter 103 enters the lens 104. The laser light that has been refracted at the lens 104 is incident on the reference sample 120, The lens 104, which is disposed between the beam splitter 103 and the objective lens 106, concentrates the laser light. Further, a transparent reference sample 120 is disposed at the light-concentration point formed by the lens 104. Part of the incident light incident on the reference sample 120 is Raman-scattered. This Raman scattered light has a different wavelength from the laser wavelength due to the Raman shift. Note that the reference sample 120 is made of a substance whose Raman spectrum is known. Therefore, the Raman scattered light generated in the reference sample 120 serves as a reference light. Examples of the reference sample 120 include a solid substance such as quart; sapphire, diamond, PET (polyethylene terephthalate), polyethylene, acryl, polycarbonate, and Dahl. Alternatively, a liquid substance (including a mixture) such as ethanol and carbon tetrachloride may be used as the reference sample 120. Further, a gas substance, such as nitrogen and oxygen, encapsulated in a chamber may be used as the reference sample 120.

A substance having a Raman peak at a position that is close to the Raman peak of the measurement sample 121 but does not overlap the Raman peak of the measurement sample 121 is preferably used as the reference sample 120. For example, quartz, which has a plurality of Raman peaks in 0 to 1500 $cm^{-1}$ and whose peak positions are precisely known, is suitable as a reference sample 120 in a ease where the stress and/or the temperature of a semiconductor device made of Si for made of other substances such as SiGe as SiC) having a peak at 520 cm-1 is measured. The light that has passed through the reference sample 120 becomes collimated. The light again by the lens 105, which is disposed between the reference sample 120 and the objective lens 106, and then enters the objective lens 106. By using the optical system like this, it is possible to perform simultaneous measurement of the reference sample 120 (measurement of a spectrum in which spectrums of the measurement sample 121 and the reference sample 120 are superimposed on each other) without splitting the laser beam. Further, by using a transparent reference sample 120 it is possible to minimize the losses of the laser light and the Raman scattered light from the measurement sample 121.

The laser light refracted at the lens 105 enters the objective lens 106. The objective lens 106 concentrates the light beam and makes the light beam incident on the measurement sample 121. That is, the objective lens 106 concentrates the light beam on the measurement sample 121 and thereby illuminates the measurement sample 121. As a result, a spot-like area is illuminated on the measurement sample 121.

Part of the incident light incident on the measurement sample 121 is Raman-scattered. Part of the incident light incident on the measurement sample 121 that is emitted to the objective lens 106 side by the Raman scattering is defined as outgoing light. That is, part of the Raman scattered light that enters the objective lens 106 is defined as the outgoing light from the measurement sample 121. The outgoing light from the measurement sample 121 has a different wavelength from that of the incident light. That is, the outgoing light from the measurement sample 121 is scattered while its frequency is shifted due to the Raman shift. The spectrum of the outgoing light from the measurement sample 121 becomes the Raman spectrum of the measurement sample 121.

The outgoing light from the measurement sample 121 enters the objective lens 106. Therefore, the outgoing light from the measurement sample 121 propagates through the same optical path as the incident light. That is, the outgoing light from the measurement sample 121 is refracted by the objective lens 106 and enters the lens 105. Further, the outgoing light from the measurement sample 121 is refracted at the lens 105 and passes through the reference sample 120. Then, the outgoing light is refracted at the lens 104 and is incident on the bean splitter 103.

Further, part of the Raman scattered light generated in the reference sample 120 is also incident on the beam splitter 103 through the lens 104. Note that when the measurement sample 121 is made of a substance that reflects laser light, Raman scattered light is also generated by the laser light reflected on the measurement sample 121. Note that part of the Raman scattered light generated in the reference sample 120 that heads for the lens 104 is defined as the outgoing light from the reference sample 120. Note that the outgoing light from the reference sample 120 includes the Raman scattered light that is generated in the reference sample 120 toward the measurement sample 121 and reflected on the measurement sample 121. The outgoing light from the reference sample 120 has a different wavelength from the laser wavelength. Similarly to the outgoing light from the measurement sample 121, the outgoing light from the reference sample 120 enters the lens 104. The outgoing light from the reference sample 120 and the outgoing light from the measurement sample 121 are combined with each other. The outgoing light from the reference sample 120 and the outgoing light from the measurement sample 121 propagate through the same optical path.

The lens 104 converts the outgoing light from the measurement sample 121 and the outgoing light from the reference sample 120 into collimated light. Then, the outgoing light refracted at the lens 104 is incident on the beam splitter 103. The beam splitter 103, which is a dichroic mirror, separates the laser light and the Raman scattered light based on the wavelength difference. That is, the outgoing light from the measurement sample 121 is split from the incident light that is emitted from the laser light source 101 and is incident on the measurement sample 121. The beam splitter 103 is disposed in such a manner that its reflection plane is inclined with respect to the optical axis of the incident light. Since the outgoing light from the measurement sample 121 is reflected on the beam splitter 103, the optical axis of the outgoing light from the measurement sample 121 is changed from the optical axis of the incident light that is emitted from the laser light source 101 and is incident on the measurement sample 121. Therefore, it is possible to separate the outgoing light emitted from the measurement sample 121 from the incident light that is emitted from the laser light source 101 and is incident on the measurement sample 121. Similarly, the outgoing light from the reference sample 120 is separated from the incident light that is emitted from the laser light source 101 and is incident on the measurement sample 121. In this way, the optical path of the incident light that is heading from the laser light source 101 toward the measurement sample 121 and the optical path of the outgoing light that is heading from the measurement sample 121 or the reference sample 120 toward the spectroscope 109 are separated from each other.

The beam splitter 103, which is a dichroic mirror, has such a characteristic that the beam splitter 103 lets light having a laser wavelength pass therethrough and reflects Raman scattered light. That is, by using a dichroic mirror as the beam splitter 103, it is possible to eliminate Rayleigh scattered light based on the wavelength difference between the Rayleigh scattered light and the Raman scattered light. Further, most of the laser light from the laser light source 101 passes through the beam splitter 103 and heads for the reference sample 120 and the measurement sample 121. As a result, it is possible to reduce the loss of the laser light and thereby detect only the Raman scattered light with efficiency. Note that the reflection property of the dichroic mirror may be determined according to the range of spectrums to be measured.

The outgoing light reflected on the beam splitter 103 enters the lens 107. The lens 107 concentrates the outgoing light on the entrance slit 108 disposed on the incident side of the spectroscope 109. The lens 107 refracts the outgoing light and thereby forms an image on the entrance slit 108. Note that since the incident light is formed into a spot-like image on the surface of the measurement sample 121, the outgoing light is concentrated into a spot-like shape on the entrance slit 108. The outgoing light that has passed through the opening of the entrance slit 108 enters the spectroscope 109.

This outgoing light, which has passed the entrance slit 108, enters the spectroscope 109. The spectroscope 109 includes a dispersive element such as a diffraction grating (grating) or a prism, and spatially disperses the incident light from the entrance slit 108 according to its wavelength. When the spectroscope 109 uses a reflection grating, the spectroscope 109 further includes an optical system including a concave mirror that guides the light from the entrance slit 108 to the dispersive element and another concave mirror that guides the light that is dispersed by the dispersive element to the detector 110. Needless to say, a spectroscope 31 having a configuration other than the configuration described above may be also used. The outgoing light is dispersed by the spectroscope 109 in a direction perpendicular to the direction of the entrance slit 108. That is, the spectroscope 109 wavelength-disperses the outgoing light in a direction perpendicular to the line-like opening of the entrance slit 108. The outgoing light that is dispersed by the spectroscope 109 enters the detector 110. The detector 110 is an area sensor in which light-sensitive elements are arranged in a matrix. Specifically, the detector 110 is a two-dimensional array photodetector, such as s two-dimensional CCD camera, in which pixels are arranged in an array.

The pixels of the detector 110 are arranged along a direction corresponding to the entrance slit 108. Therefore, one of the array directions of the pixels of the detector 110 conforms to the direction of the entrance slit 108 and the other array direction conforms to the dispersion direction of the spectroscope 109. The direction corresponding to the direction of the entrance slit 108 of the detector 110 is defined as a Y-direction and the direction perpendicular to the entrance slit 108, i.e., the direction in which the outgoing light is dispersed by the spectroscope 109 is defined as an X-direction. Therefore, the wavelength of the Raman scattered light corresponds to a position in the X-direction on the light-receiving surface of the detector 110. That is, different pixels arranged in the X-direction detect Raman scattered lights having different wavelengths. Therefore, it is possible to measure a Raman spectrum by one frame of the detector 110. Note that a pinhole may be used in place of the entrance slit 108.

The detector 110 outputs a detection signal(s) according to the light intensity of the outgoing light received at each pixel to a processing device 111. The processing device 111 is, for example, an information processing device such as a personal computer (PC), and stores the detection signal(s) supplied from the detector 110 into a memory or the like. In this way, it is possible to measure a Raman spectrum. The Raman spectrum of the reference sample 120 is known in advance. The spectrum information of the reference sample 120 is stored in the processing device 111. By referring this spectrum information, it is possible to extract the peak position(s) of the Raman scattered light from the reference sample 120 based on the peak position(s) (peak wavelength(s)) of the measured Raman spectrum. Further, it is possible to distinguish between the peak position of the reference sample 120 and the peak position of the measurement sample 121 based on the peak position of the measured Raman spectrum.

Specifically, the peak position of the measured spectrum is determined. For example, fitting is performed for the measured spectrum data with a known Gaussian function or a Lorentz function. By doing so, it is possible to automatically extract the peak position. Then, it is determined whether or not the extracted peak position is the Raman peak generated by the reference sample 120 based on the spectrum information of the reference sample 120, which has been stored in advance. In this example, it is possible to determine that the peak position of the measured spectrum that is close to the peak position in the spectrum information is the Raman peak of the reference sample 120. Then, the peak position other than the Raman peak of the reference sample 120 is determined to be the Raman peak of the measurement sample 121. In this way, it is possible to specify each of the peak position of the reference sample 120 and the peak position of the measurement sample 121.

The peak position of the Raman spectrum of the reference sample 120 and the peak position of the Raman spectrum of the measurement sample 121 are compared with each other. By obtaining the difference between the peak positions, it is possible to calibrate the peak position of the measurement sample. Then, it is possible to measure the stress and/or the temperature of the measurement sample 121 based on this comparison result. Further, by scanning the laser light by using a stage, a scanner, or the like, it is possible to measure the stress distribution and/or the temperature distribution in the measurement sample 121. Further, it is possible to measure the peak shift of the Raman peak and thereby perform peak shift imaging.

By using the Raman scattered light from the reference sample 120 as a reference light as described above, it is possible to carry out highly accurate measurement. Further, since all it takes is to add the lens 104 and the lens 105, the measurement can be carried out with ease. It is possible to use the common optical path for both the reference sample 120 and the measurement sample 121. As a result, it is possible to reduce the loss in the amount of light that is caused by, the splitting of the light beam.

Further, it is possible to determine the peak position of the measurement sample 121 by using a plurality of peaks of the reference sample 120. For example, assume that the measurement results of the peak positions of the reference sample are represented by $P_{r1}$ and $P_{r2}$ and the corresponding known peak positions of the reference sample are represented by $P_{k1}$ and $P_{k2}$, in this case, a function y=f(x) that expresses a relation between a peak position x of the measurement result and a calibrated peak position y can be obtained as a straight line that passes through the point ($P_{k1}$, $P_{k2}$) and the point ($P_{r1}$, $P_{r2}$). When the peak position of the measurement sample is represented by $P_m$, the calibrated peak position $P_{ca1}$ can be obtained, by using the function f, as $P_{ca1}=f(P_m)$.

Needless to say, the peak position of the measurement sample 121 may be obtained by using three or more peaks. In such a case, the function f may be a straight line, or may be an appropriate function determined based on the characteristics of the spectroscope, obtained from known peak positions of the reference sample and peak positions of the measurement result by using a least-squares method. Note that values that are calibrated in advance based on the characteristics of the spectroscope or the like may be used as peak positions of the measurement result of the reference sample and the measurement sample.

The reference sample 120 can be removably disposed on the optical path. In this way, it is possible to carry out measurement by selecting a suitable reference sample 120 for the measurement sample 121, and to carry out measurement by using the measurement sample 121 alone. That is, when measurement is carried out by using the measurement sample 121 alone, the reference sample 120 is removed from the optical path of the laser light. Further, when the measurement sample 121 is changed, a suitable reference sample 120 for the new measurement sample 121 is disposed on the optical path. In this manner, it is possible to change the reference sample 120 according to the measurement sample 121. By selecting a suitable reference sample 120 for the measurement sample 121, it is possible to carry out measurement with higher accuracy.

Figure 2:
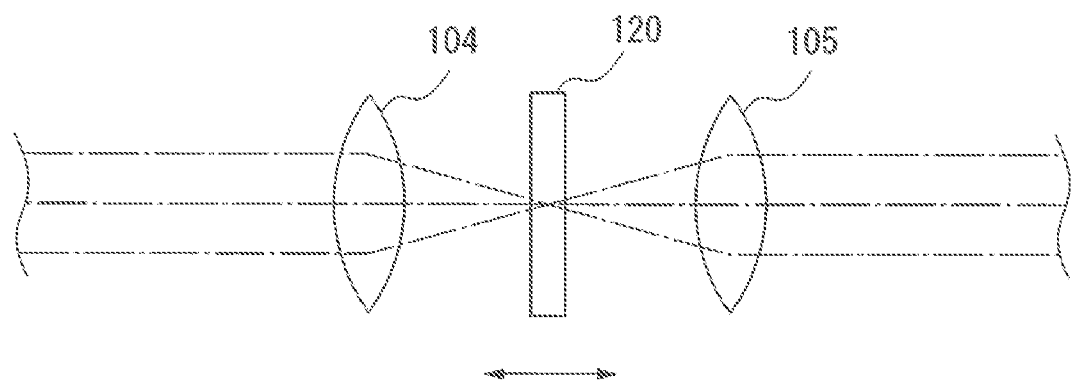
FIG. 2 shows an arrangement of a reference sample and lenses.

Further, the optical system in the spectrometry device 100 is a confocal optical system. Therefore, it is possible to adjust the intensity of the Raman scattered light from the reference sample 120 by moving the reference sample 120. As shown in FIG. 2, the reference sample 120 is movable along the optical axis. The laser light source 101 and the reference sample 120 are disposed in mutually conjugate positions, and the reference sample 120 and the entrance slit 108 are disposed in mutually conjugate positions. Therefore, as the reference sample 120 moves along the optical axis, the reference sample 120 is deviated from the focal point of the lens 104 or the lens 105. Further, as the reference sample 120 is deviated from the focal point, the image-forming position of the reference sample 120 is deviated from the entrance slit 108. Therefore, the light that passes through the entrance slit 108 becomes weaker. In this manner, it is possible to adjust the intensity of the Raman scattered light (reference light) from the reference sample 120.

Raman spectrums of the measurement sample 121 and the reference sample 120 are compared with each other. Therefore, it is possible to precisely determine a peak position even in the cases where the wavelength of the laser light fluctuates during the measurement. This is because since the difference between the wavenumber of the Raman scattered light and the wavenumber of the light source reflects the sample, both of the wavenumbers of the measurement sample and the reference sample change by the same amount even if the wavelength (wavenumber) of the laser light fluctuates. When a quality laser light source is used, the oscillation wavelength may not be stabilized. Even in such a case, it is possible to prevent the accuracy of peak position measurement from deteriorating. Therefore, it is possible to use an inexpensive laser light source. Further, it is possible to improve the detection efficiency by applying an antireflective coating for increasing the transmittance of the laser light and the Raman scattered light onto the reference sample 120.

Note that although a substance whose Raman spectrum is known is used as the reference sample 120, a substance whose Raman spectrum is not known in advance may be also used for the reference sample 120. In such a case, the Raman spectrum of the reference sample 120 may be measured before or after the measurement of the measurement sample 121. For example, the peak position(s) of the reference sample 120 is measured by using a light source whose spectrum is known such as a neon lamp before the measurement of the measurement sample 121. The peak position(s) of the reference sample 120 is measured in advance by using a light source whose peak position in the spectrum is known. In this way, the peak position(s) in the Raman spectrum of the reference sample 120 becomes known.

Second Exemplary Embodiment

Figure 3:
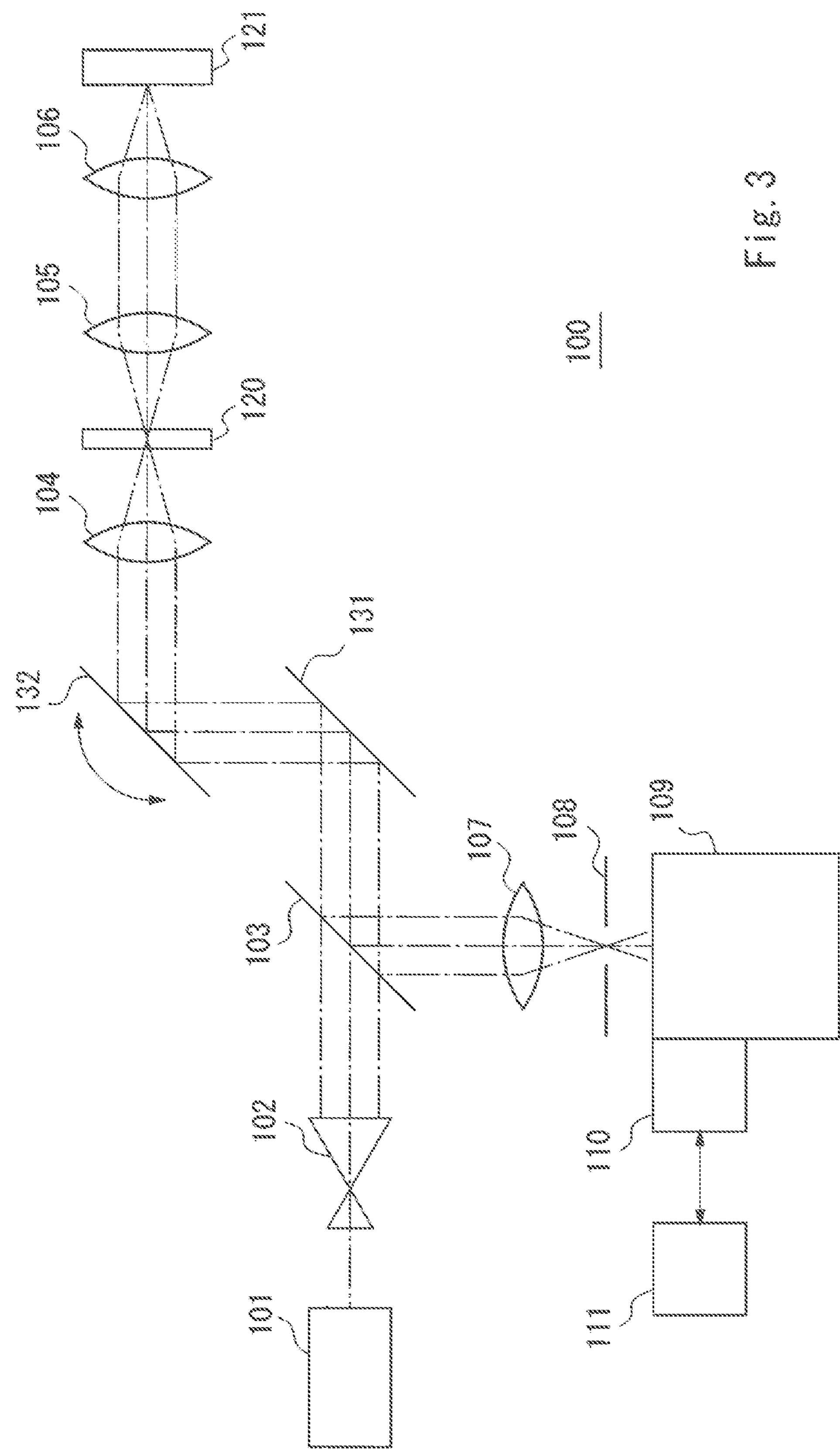
FIG. 3 shows a configuration of a spectrometry device according to a second exemplary embodiment.

A spectrometry device according to this exemplary embodiment is explained with reference to FIG. 3. FIG. 3 shows a configuration of a spectrometry device 100. In this exemplary embodiment, an optical scan system using a galvano-mirror is added to the optical system of the spectrometry device shown in the first exemplary embodiment. Therefore, in FIG. 3, a mirror 131 and a galvano-mirror 132 are added in the spectrometry device 100 shown in FIG. 1. Note that explanation of the components/configurations that are the same as those of the first exemplary embodiment is omitted as appropriate.

The mirror 131 and the galvano-mirror 132 are disposed between the beam splitter 103 and the lens 104. Therefore, the laser light that has passed through the beam splitter 103 is reflected on the mirror 131 and is incident on the galvano-mirror 132. Since the galvano-mirror 132 deflects the laser light, the incident position of the laser light on the measurement sample 121 is changed. That is, as the reflection angle of the laser light by the galvano-mirror 132 changes, the laser light is scanned over the measurement sample. Further, the incident position of the laser light on the reference sample 120 is also changed. In this way, the galvano-mirror 132 scans the laser light. Further, the outgoing light from the reference sample 120 and the measurement sample 121 is descanned in the galvano-mirror 132 and is incident on the mirror 131. Then, the outgoing light from the reference sample 120 and the measurement sample 121 is reflected on the mirror 131 and is incident on the beam splitter 103.

In this optical system, the reference sample 120 is disposed at the focal point (hereinafter called intermediate image plane) of the relay lenses (lens 104 and lens 105). By using this configuration, Raman spectrums of the reference sample 120 and the measurement sample 121 can be simultaneously measured without using any additional optical system. That is, Raman scattered lights of the reference sample 120 and the measurement sample 121 can be simultaneously measured just by disposing the reference sample 120 at the intermediate image plane, which already exists. Therefore, it is possible to carry out highly accurate measurement with ease.

Figure 4:
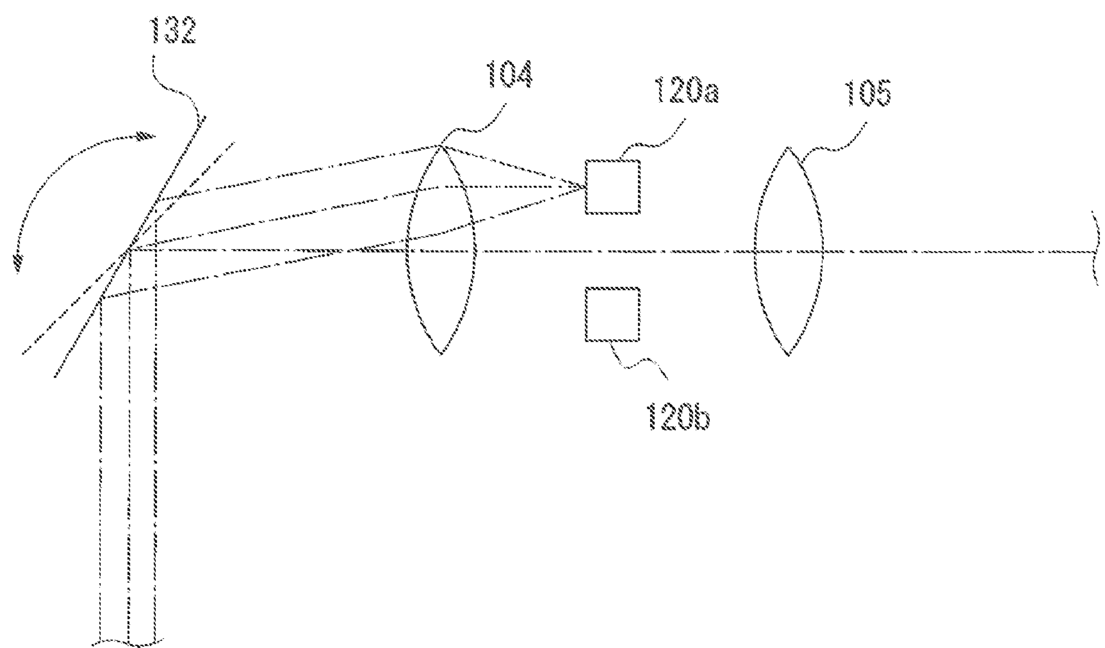
FIG. 4 shows an arrangement example of a reference sample in a spectrometry device according to a second exemplary embodiment.

In the spectrometry device including the optical scan system using the galvano-mirror 132, it is also possible to adopt such a configuration that the measurement of the reference sample 120 and the measurement of the measurement sample 121 are switched. This configuration is explained with reference to FIG. 4. FIG. 4 schematically shows a configuration between the lens 104 and the lens which are relay lenses.

In this configuration, the reference sample 120 is disposed Out of the optical axis of the lens 104 and the lens 105. That is, the reference sample 120 is not disposed on the optical axis of the lens 104 and the lens 105. As shown in FIG. 4, reference samples 120*a*, and 120*b* are disposed on both sides of the optical axis (alternate long and short dash line in FIG. 4). Further, the optical axis passes through between the reference samples 120*a* and 120*h*. Therefore, when the light-concentration point of the lens 104 is located on the optical axis of the lens 104, the laser light is not incident on the reference samples 120*a* and 120*b*. In this case, the laser light is incident on the measurement sample 121. By the scanning performed by the galvano-mirror 132, the light-concentration point of the laser light by the lens 104 is deviated from the optical axis. That is, when the laser light is deflected by the galvano-mirror 132, the laser light is incident on the reference sample 120*a* or 120*b*. In this manner, as the deflection angle is changed by the galvano-mirror 132, the laser light is incident on these samples in the order of the reference sample 120*a*, the measurement sample 121 (between the reference samples 120*a* and 120*b*), the reference sample 120*h*, and the measurement sample 121 (between the reference samples 120*a* and 120*b*). Therefore, it is possible to switch the measurement between the measurement of the reference sample 120 and the measurement of the measurement sample 121 by changing the deflection angle. Further, in this ease, an opaque sample such as a silicon crystal can be used as the reference sample 120*a* and the reference sample 120*b*.

In the configuration shown in FIG. 4, it is also possible to measure a spectrum in which Raman spectrums of the measurement sample 121 and the reference sample 120 are superimposed on each other.

The scanning cycle of the galvano-mirror 132 is made sufficiently short with respect to the exposure time of the detector 110, That is, the galvano-mirror 132 is moved at high speed during one exposure of the detector 110. For example, for the exposure time of 1 sec, the moving time of the laser spot by the galvano-mirror is adjusted to 10 msec. When one second is required for the measurement of one point on the measurement sample 121, the first 490 msec is spent for the measurement of the measurement sample 121. That is, one point (x.n, y) on the measurement sample 121 is illuminated for 490 msec without moving the galvano-mirror 132. Then, the galvano-mirror 132 is operated for 10 msec and the laser spot is thereby moved from the measurement sample 122 to the reference sample 121. Then, the next 490 msec is spent for the measurement of the reference sample 120. That is, one point on the reference sample 120 is illuminated for 490 msec without moving the galvano-mirror 132, Further, in the next 10 msec, the laser spot is moved to another one point (x_n+1, y) on the measurement sample 121, By repeating these operations, the measurement is performed for a predetermined area of the measurement sample 121. Note that the point in the reference sample 120 that is irradiated with the laser light may be unchanged throughout the whole measurement, or may be changed for each measurement in consideration of the damage caused by the laser irradiation.

In this way, it is possible to obtain a spectrum in which Raman spectrums of the reference sample 120 and the measurement sample 121 are superimposed on each other. It is possible to reduce the time between the measurement of the reference sample 120*a* or 120*b* and the measurement of the measurement sample 121. For example, it is possible to perform the measurement of the measurement sample 121 immediately after the measurement of the reference sample 120*a* or 120*b*.

Then, each peak position is obtained from the measured spectrum. By obtaining the difference in peak position between the measurement sample 121 and the reference sample 120, it is possible to measure the stress, the temperature, and/or the like with high accuracy. Since the galvano-mirror 132 deflects the light beam, the light beam that is originally incident on the measurement sample 121 is incident on the reference sample 120. By doing so, it is possible to use a non-transparent reference sample 120. Needless to say, the light beam may be deflected by using optical scan means other than the galvano-mirror 132. Note that when only the Raman spectrum of the measurement sample 121 is measured, the optical system may be configured so that the scanning is not performed. Alternatively, the scanning may be performed in the range in which the incident light is not incident on the reference samples 120*a* and 120*b*. Note that as for the reference sample 120*a* or 120*b* , in addition to the sample that generates Raman scattered light, a light source whose wavelength is known such as a neon lamp, a mercury lamp, and an argon lamp may be disposed and thereby used for the calibration of the spectrum.

Further, the scanning may be performed in the XY-directions by the galvano-mirror 132. For example, the gaivano-mirror 132 may be composed of a pair of galvano-mirrors, An X-direction galvano-mirror and a Y-direction galvano-mirror are disposed. Then, two-dimensional scanning is performed by the galvano-mirror pair. In this way, a two-dimensional Raman image can be obtained. For example, XY Open Frame available from Cambridge Technology (Cambridge Technology) may be used as a two-axis galvano-mirror for scanning in XY-directions (see http://www.gsig.co.jp/precision/products 03.html). Alternatively, scanning along one axis may be performed by the galvano-mirror 132 and scanning along the other axis may be performed by stage driving, in this manner, it is also possible to obtain a two-dimensional Raman image.

Third Exemplary Embodiment

Figure 5:
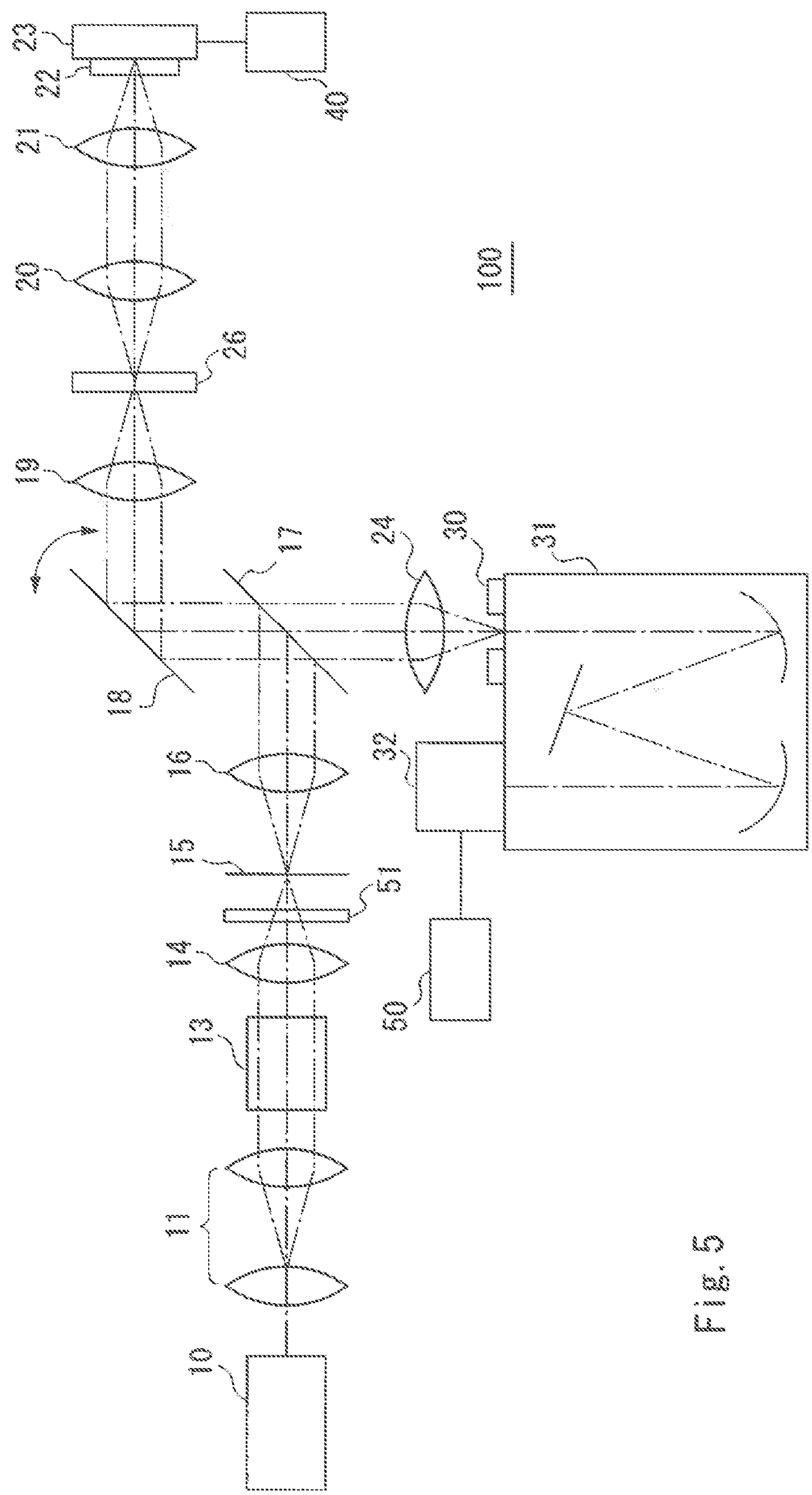
FIG. 5 shows a configuration of a spectrometry device according to a third exemplary embodiment.

A spectrometry device according to this exemplary embodiment is explained with reference to FIG. 5. In this exemplary embodiment, a reference sample 26 is disposed in the optical system shown in FIG. 7 of Patent literature 1. Note that explanation of the components/configurations that are the same as those of the first or second exemplary embodiment and the components/configurations that are the same as those of Patent literature 1 is omitted as appropriate.

A spectrometry device 100 includes, as a configuration for observing a measurement sample 22, a laser light source 10, a beam expander 11, a Y-scan device 13, a lens 14, an iris 15, a lens 16, a beam splitter 17, an X-scan mirror 18, a lens 19, a lens 20, an objective lens 21, a stage 23, a lens 24, an spectroscope 31, a detector 32, a stage drive device 40, and a processing device 50. Further, the spectroscope 31 includes an entrance slit 30 on the incident side. The reference sample 26 is disposed between the lens 19 and the lens 20. That is, the reference sample 26 is disposed at the light-concentration point of the lens 19.

Similarly to the first and second exemplary embodiments, the spectrometry device 100 is a Raman microscope, and makes a light beam from the laser light source 10 incident on the measurement sample 22 and detects Raman scattered light from the measurement sample 22 by the detector 32. Further, it can measure a Raman spectrum because the Raman scattered, light is dispersed by the spectroscope 31. Further, in the spectrometry device 100, since scanning can be performed in the XY-directions (horizontal directions) and in the Z-direction (vertical direction), as three-dimensional Raman spectrum image can be measured. Further, in this exemplary embodiment, the laser light is converted into a line-like spot and line illumination is thereby performed. Further, in this exemplary embodiment, the spectrometry device 100 constitutes a line confocal optical system.

Firstly, an overall configuration of the spectrometry device 100 is explained. The laser light source 10 emits monochromatic laser light. For example, Torus available from Laser Quantum Ltd. can be used for the laser light source 10. This laser light source 10 is a laser that has a maximum output of 400 mW and emits laser light having a laser wavelength 532 nm and a line width of 1 MHz. The laser light source 10 emits laser light having this laser wavelength. The need to use a large laser light source such as an argon laser is eliminated, and thus making it possible to reduce the apparatus in size.

The light beam from the laser light source 10 is expanded by the beam expander 11 and enters the Y-scan device 13. The Y-scan device 13 is, for example, an acoustooptical element or a galvano-mirror, and deflects an incident light beam by changing the outgoing angle of the incident light beam. In this way, the incident position of the light beam on the measurement sample 22 is changed along the Y-direction. That is, the Y-scan device 13 scans the light beam in the Y-direction. Note that the deflection angle at the Y-scan device 13 is controlled by an electric signal supplied from the processing device 50. The light beam deflected at the Y-scan device 13 is refracted at the lens 14 and is thereby incident on a cylindrical lens 51.

The cylindrical lens 51 a concave lens. The refraction in the X-direction caused by the lens 14, which is a convex lens, is cancelled out by this cylindrical lens 51. Therefore, the beam spot expands in the X-direction and thereby has an ellipse shape on the measurement sample 22. The laser light refracted at the cylindrical lens 51 enters the iris 15. Note that the lens 14 concentrates the light beam on the surface of the iris 15. The iris 15 has a predetermined aperture and blocks out the light, beam incident on the outside of the aperture. That is, it restricts the passage of the light beam outside the aperture.

The light beam that has passed through the iris 15 is refracted at the lens 16 and enters the beam splitter 17. The beam splitter 17 is, for example, dichroic mirror, and reflects light having a laser wavelength toward the measurement sample 22. For example, an edge filter available from Semrock, Inc, can be used as the dichroic mirror. The light reflected by the beam splitter 17 is incident on the X-scan mirror 18. The X-scan mirror 18 is, for example, a galvano-mirror, and deflects the light beam by changing the angle of the reflection surface. That is, since the inclination angle of the reflection surface of the X-scan mirror 18 changes with respect to the optical axis, the outgoing angle of the light beam can be changed. In this way, the incident position of the light beam on the measurement sample 22 is changed along the X-direction, in this way, it is possible to scan the light beam in the X-direction. The laser light having the spot expanded in the X-direction is scanned in the X-direction and applied to the measurement sample 22. The direction of the expansion caused by the cylindrical lens 51 is the same as the scanning direction of the X-scan mirror 18. That is, the X-scan mirror 18 scans the laser light in the direction in which the laser light is expanded by the cylindrical lens 51. Note that the deflection angle at the X-scan mirror 18 is controlled by an electric signal supplied from the processing device 50. Further, since the X-direction and the Y-direction are perpendicular to each other, the scanning can be performed in a two-dimensional area on the measurement sample 22 by performing the scanning in the XY-directions by using the X-scan mirror 18 and the Y-scan device 13.

The light beam that is scanned by the X-scan mirror 18 is refracted at the lens 19 and the lens 20, and thereby enters the objective lens 21. Further, similarly to the first and second exemplary embodiments, a reference sample 26 is disposed between the lens 19 and the lens 20. The Raman spectrum of the reference sample 26 is known and its spectrum information is stored in the processing device 50. Similarly to the above-described example, Raman scattered light is generated by this reference sample 26. The laser light that passes through the reference sample 26 and is refracted at the lens 19 enters the objective lens 21.

The objective lens 21 concentrates the light beam and makes the light beam incident on the measurement sample 22. That is, the objective lens 21 concentrates the light beam on the measurement sample 22 and thereby illuminates the measurement sample 22. As a result, a spot-like area is illuminated on the measurement sample 22. For example, Apochromat 1.2×60 available from Nikon Corporation can be used for the objective lens 21.

Part of the incident light incident on the measurement sample 22 is Raman-scattered. The Raman scattered light generated in the measurement sample 22 enters the spectroscope 31 as an outgoing light. By scanning the focal point of the incident light in the XYZ-directions and thereby measuring the spectrum of the outgoing light emitted from the entire or part of the surface of the measurement sample 22, it is possible to carry out three-dimensional measurement of the Raman spectrum.

Note that the measurement sample 22 is placed on the stage 23. The stage 23 is, for example, an XYZ-stage. This stage 23 is driven by the stage drive device 40. By driving the stage 23 in the XY-directions by the stage drive device 40, it is possible to illuminate an arbitrary area of the measurement sample 22. Further, by driving the stage in the Z-direction by the stage drive device 40, it is possible to change the distance between the objective lens 21 and the measurement sample 22. Therefore, it is possible to change the focal point of the objective lens 21 along the optical axis direction. Since the spectrometry device 100 according to the present invention constitutes a laser confocal microscope as described later, it is possible to perform scanning in the Z-direction by changing the focal point. That is, by moving the stage in the Z-direction, it is possible to take a tomographic image of the measurement sample 22. It is possible to detect Raman scattered light that is emitted from an arbitral height of the measurement sample 22 and thereby measure a three-dimensional Raman spectrum image. The processing device 50 supplies a control signal(s) to the stage drive device 40 and thereby controls the driving of the stage 23.

The outgoing light that is Raman-scattered in the measurement sample 22 placed on the stage 23 and then enters the objective lens 21 propagates through the same optical path as that of the incident light. That is, the outgoing light is refracted by the objective lens 21 and refracted by the lens 20 and the lens 19, and is incident on the X scan mirror 18. Similarly, the outgoing light from the reference sample 26 is incident on the X-scan mirror 18. The X-scan mirror 18 reflects the outgoing light that is incident on the X-scan mirror 18 toward the beam splitter 17. In this process, the outgoing light is descanned by the X-scan mirror 18. That is, by reflecting the outgoing light on the X-scan mirror 18, the outgoing light propagates in the opposite direction to the traveling direction of the incident light that is emitted from the laser light source 10 and is incident on the X-scan mirror 18. Further, Rayleigh scattered light from the measurement sample 22 also propagates through the same optical path as that of the Raman scattered light.

The outgoing light reflected by the X-scan mirror 18 enters the beam splitter 17. The beam splitter 17 is, for example, a dichroic mirror, and separates the outgoing light from the reference sample 26 and the measurement sample 22 and the incident light that is emitted from the laser light source 10 and is incident on the measurement sample 22 based on the wavelength. That is, the beam splitter 17 is disposed in such a manner that its reflection plane is inclined with respect to the optical axis of the incident light. Since the outgoing light from the measurement sample 22 passes through the beam splitter 17, the optical axis of the outgoing light from the measurement sample 22 is changed from the optical axis of the incident light that is emitted from the laser light source 10 and is incident on the measurement sample 22. Therefore, it is possible to separate the outgoing light emitted from the reference sample 26 and the measurement sample 22 from the incident light that is emitted from the laser light source 10 and is incident on the measurement sample 22.

Further, the beam splitter 17, which is a dichroic mirror, has such a characteristic that the beam splitter 17 reflects light having a laser wavelength and lets Raman scattered light pass therethrough. Therefore, the Rayleigh scattered light from the reference sample 26 and the measurement sample 22 is reflected on the beam splitter 17, and the Raman scattered light having a different wavelength passes through the beam splitter 17. That is, by using a dichroic mirror as the beam splitter 17, it is possible to eliminate the Rayleigh scattered light based on the wavelength difference between the Rayleigh scattered light and the Raman scattered light. Further, most of the laser light from the laser light source 10 is reflected on the beam splitter 17 and heads for the measurement sample 22. As a result, it is possible to reduce the loss of the laser light and thereby detect only the Raman scattered light with efficiency. Note that the reflection property of the dichroic mirror may be determined according to the range of spectrums to be measured. Note that the beam splitter 17 is disposed between the measurement sample 22 and the Y-scan device 13. Therefore, the beam splitter 17 separates the outgoing light that has not yet been descanned by the Y-scan device 13 from the light beam from the laser light source 10.

The outgoing light that has passed through the beam splitter 17 is refracted at the lens 24 and enters the entrance slit 30 disposed on the incident side of the spectroscope 31. At this point, the lens 24 concentrates the outgoing light on the entrance slit 30. That is, the lens 24 forms an enlarged image of an illuminated area of the measurement sample 22 on the entrance slit 30. A line-like opening is formed in the entrance slit 30. This opening is formed along a direction corresponding to the Y-direction. That is the opening of the entrance slit 30 is formed in a direction corresponding to the scanning direction of the Y-scan device 13 (Y-direction) on the measurement sample 22.

The lens 24 refracts the outgoing light and thereby forms an image on the entrance slit 30. Note that since the incident light is formed into a line-like image on the illuminated plane of the measurement sample 22, the outgoing light is concentrated into a line-like shape on the entrance slit 30. The direction of the opening of the entrance slit 30 is conformed to the scanning direction of the Y-scan device 13. The outgoing light enters the beam splitter 17 without being descanned by the Y-scan device 13. Therefore, when the outgoing light is scanned by the Y-scan device 13, the spot position of the light beam moves in the direction of the line-like opening of the entrance slit 30 on the entrance slit 30. The components are arranged so that the light that has been scanned in the Y-direction on the measurement sample 22 forms an image on the opening of the entrance slit 30. In other words, the entrance slit 30 and the measurement sample 22 are disposed so that they have a mutually conjugate relation. Therefore, the Raman microscope is formed as a confocal optical system. That is, the iris 15 and the illuminated plane of the measurement sample 22 are disposed so that they have a mutually conjugate relation, and the illuminated plane of the measurement sample 22 and the entrance slit 30 are disposed so that they have a mutually conjugate relation. The incident light is concentrated into a line-like shape on the XY-plane on which the iris 15 is disposed and on the illuminated plane of the measurement sample 22. Then, the outgoing light that has been scattered and emitted from the measurement sample 22 is concentrated into a line-like shape on the entrance slit 30. The entrance slit 30 has an opening formed along the Y-direction, and lets only the outgoing light that enters this opening pass therethrough to the detector 32 side. By forming each of the illumination optical system from the laser light source 10 to the measurement sample 22 and the observation optical system from the measurement sample 22 to the detector 32 as an image-forming optical system as described above, it is possible to form a confocal Raman microscope. As a result, pt is possible to carry out measurement in the Z-direction with a high resolution. Further, by moving the stage 23 in the Z-direction, it is possible to separate Raman scattered light emitted from an arbitral height of the measurement sample 22 from Raman scattered light emitted from other heights and detect the separated Raman scattered light.

The outgoing light that has passed through the entrance slit 30 enters the main body of the spectroscope 31. The spectroscope 31 includes a dispersive element such as a diffraction grating (grating) or a prism, and spatially disperses the incident light from the entrance slit 30 according to its wavelength, in the case of a spectroscope 31 using a reflection grating, the spectroscope 31 further includes an optical system including a concave mirror that guides the light from the entrance slit 30 to the dispersive element and another concave mirror that guides the light that is dispersed by the dispersive element to the detector 32. Needless to say, a spectroscope 31 having a configuration other than the configuration described above may be also used. The outgoing light is dispersed by the spectroscope 31 in a direction perpendicular to the direction of the entrance slit 30 That is the spectroscope 31 wavelength-disperses the outgoing light in a direction perpendicular to the line-like opening of the entrance slit 30. The outgoing light that is dispersed by the spectroscope 31 enters the detector 32. The detector 32 is an area sensor in which light-sensitive elements are arranged in a matrix. Specifically, the detector 32 a two-dimensional array photodetector, such as s two-dimensional CCD camera, in which pixels are arranged in an array.

For example, a cooled CCD can be used for the detector 32 Specifically, a 1024×2.56 pixel electronic cooled CCD (−25° C.) available from Princeton Instrument can be used as the detector 32. Further, the detector 32 can be equipped with an image intensifier. The pixels of the detector 32 are arranged along a direction corresponding to the entrance slit 30. Therefore, one of the array directions of the pixels of the detector 32 conforms to the direction of the entrance slit 30 and the other array direction conforms to the dispersion direction of the spectroscope 31. The direction corresponding to the direction of the entrance slit 30 of the detector 32 is defined as a Y-direction and the direction perpendicular to the entrance slit 30, i.e., the direction in which the outgoing light is dispersed by the spectroscope 31 is defined as an X-direction. In this way, the spectrums of the outgoing lights from the reference sample 26 and the measurement sample 22 can be simultaneously measured.

The detector 33 outputs a detection signal(s) according to the light intensity of the outgoing light received at each pixel to a processing device 50. The processing, device 50 is, for example, an information processing device such as a personal computer (PC), and stores the detection signal(s) supplied from the detector 32 into a memory or the like. Then, it performs predetermined processing on the detection result and displays the processed result. Further, the processing device 50 controls the scanning of the Y-scan device 13 and the X-scan mirror 18, and controls the driving of the stage 23. Note that the X-direction of the detector 32 corresponds to the wavelength (frequency) of the outgoing light. That is, in a row of pixels arranged in the X-direction, pixels located at one end detect outgoing light having a long wavelength (low frequency) and pixels located at the other end detect outgoing light having a short wavelength (high frequency). In this manner, the distribution of light intensities in the X-direction of the detector 32 represents the distribution of a Raman spectrum.

Note that the light beam is scanned at least once in the Y-direction within the period in which the detector 12 takes images corresponding to one frame. That is, the scanning cycle of the Y-scan device 13 is made shorter than the exposure time, so that the scanning is performed at least once in the Y-direction within the exposure time for one frame of the detector 32 In this way, it is possible to measure a Raman spectrum of a line-like area corresponding to the scan range by using one frame of the detector 32. For example, even when a Raman spectrum is measured for a large three-dimensional area, it is possible to prevent the measurement time from becoming longer and thereby improve the practicality.

As described above, the spectral information of Raman scattered light is developed in a direction perpendicular to the Y-direction of the detector 32 in which the pixels are arranged in a two-dimensional array. Then, the spectral information of a straight-line area in the sample is obtained all at once. Therefore, it is possible to measure a Raman spectrum at high speed. Further, since laser light is scanned, it is possible to illuminate uniformly and thereby perform measurement with accuracy. That is, since the light is scanned at high speed, the speckle noise can be prevented. Further, since the light is scanned, it is possible to reduce fluctuations in the illumination light intensity that occur according to the position on the measurement sample 22. Therefore, it is possible to carry out accurate measurement in a short time.

In this way, it is possible to carry out a Raman spectrum of a line-like area. Then, when the above-described one frame image taking process has been finished, the illumination position is shifted by a distance equivalent to one illumination area in the X-direction by the X-scan mirror 18. Then, a Raman spectrum of a line-like area is measured by taking images corresponding to one frame in a similar manner. By repeating these processes, it is possible to measure a Raman spectrum of a two-dimensional area on the measurement sample 22, Note that since a Raman spectrum can be measured for each illumination area of the objective lens, it is possible to measure a two-dimensional Raman spectrum image. That is, since the scanning is performed in the X-direction by the X-scan mirror 18, it is possible to perform Raman spectrometry at each point of the sample. That is, it is possible to measure a Raman spectrum in a two-dimensional area on the measurement sample 22. Further, by moving the stage 23 in the XY-directions, it is possible to measure a Raman spectrum of a larger area. Further, it is possible to carry out three-dimensional measurement by moving the stage 23 in the Z-direction and thereby moving the focal point along the optical axis. That is, when the spectrum measurement of a two-dimensional area has been finished, the focal point is shifted in the Z-direction and Raman spectrum measurement of a two-dimensional area is performed in a similar manner. In this way, it is possible to perform a three-dimensional measurement of a Raman spectrum.

Figure 8:
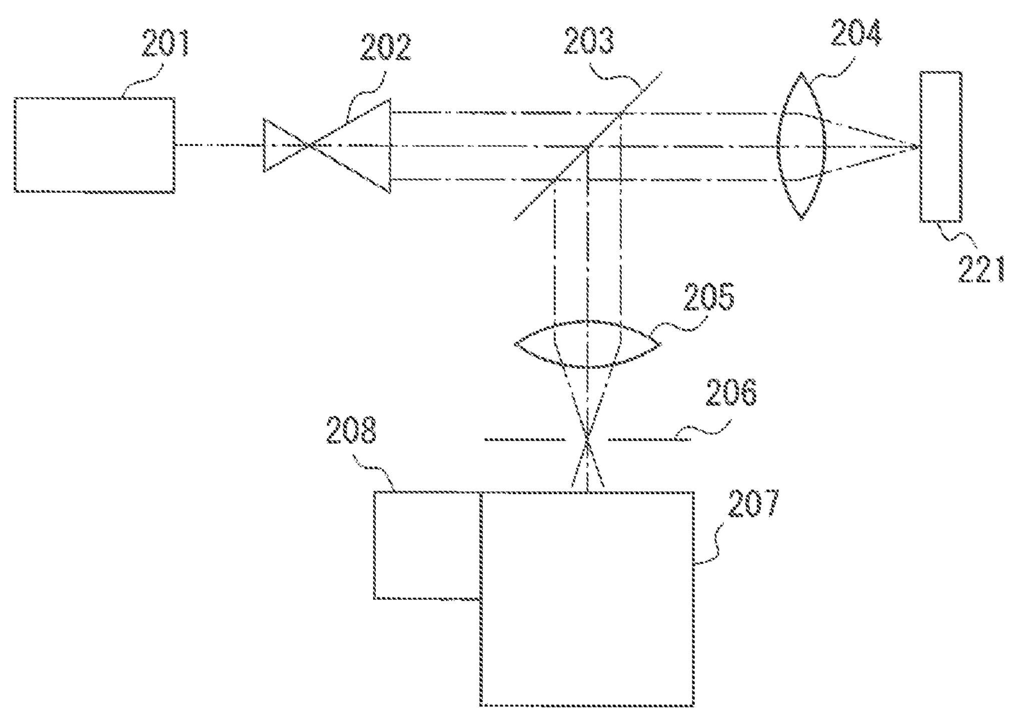
FIG. 8 shows a Raman spectrophotometer disclosed in Patent literature 2.
Figure 9:
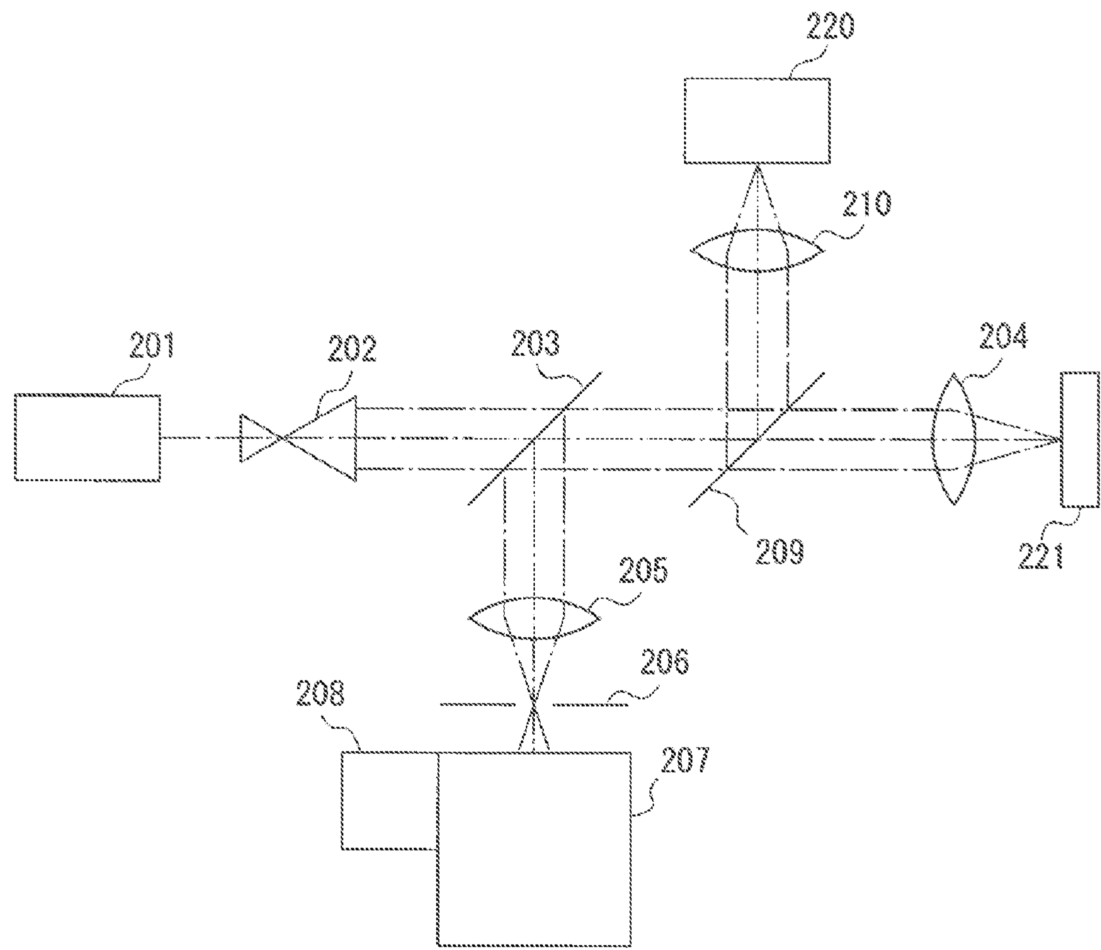
FIG. 9 shows a configuration for explaining a reference sample, in which exciting light is split.

The peak position of the reference sample 26 and the peak position of the measurement sample 22 are compared with each other at each point of the line-like shape. By doing so, it is possible to obtain a distortion amount. Note that in FIG. 8 of Patent literature 1, the light-concentration point of the lens 19 is in a vacuum in order to prevent the Raman scattered light of the air from overlapping. Alternatively, a substance that emits Raman scattered light having a different wavelength range from that of the Raman scattered light of the measurement sample 22 is disposed. That is, the Raman scattered light emitted from the substance disposed at the light-concentration point of the lens 19 is eliminated by the beam splitter 17 (dichroic mirror). In contrast to this, in this exemplary embodiment, spectrometry is carried out for Raman scattered light generated in the reference sample 26 by disposing the reference sample 26 at the light-concentration point of the lens 19. Further, by carrying out spectrometry simultaneously for the reference sample 26 and the measurement sample 22, a Raman peak(s) generated in the reference sample 26, whose spectrum information is known, is specified. A Raman peak of each of the reference sample 26 and the measurement sample 22 is determined. By doing so, it is possible to carry out measurement with higher accuracy.

When a peak position of the reference sample 26 and a peak position of the measurement sample 22 are compared with each at each point on the line by using line illumination, there is a possibility that the measurement result of the peak position is affected by the sensitivity variations of the pixels (pixels) of the detector 32. In such cases, it is possible to reduce the effect caused by the sensitivity variations by carrying out the measurement of the reference sample 26 and the measurement sample 22 a plurality of times.

Figure 6A:
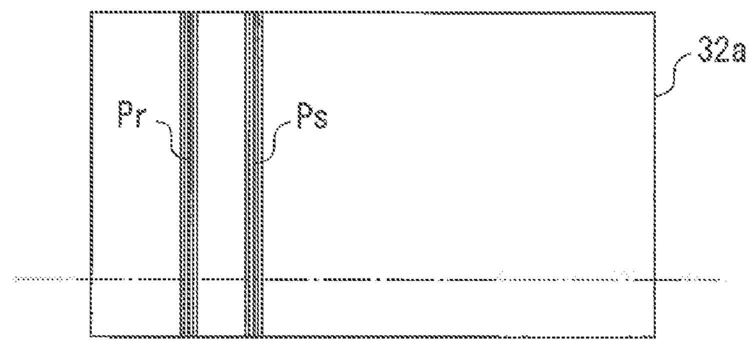
FIG. 6A is a figure for explaining a principle for measuring a pea position in a spectrum.
Figure 6B:
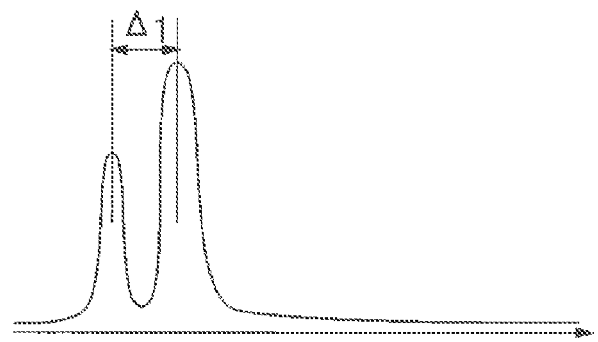
FIG. 6B is a figure for explaining a principle for measuring a peak position in a spectrum.

For example, as shown in FIG. 6A, Raman scattered lights from the reference sample 26 and the measurement sample 22 are simultaneously measured by the detector 32. Note that FIG. 6A schematically shows a light-receiving surface 32*a* of the detector 32. In FIG. 6A, the horizontal direction corresponds to the wavelength direction of the spectrum. There are the incident position Pr of the Raman peak of the reference sample 26 and the incident position Ps of the Raman peak of the measurement sample 22 in this light-receiving surface 32*a*. In the light-receiving surface 32*a*, columns of pixels along the Y-direction correspond to the incident position Pr and the incident position Ps, and the incident position Pr and the incident position Ps correspond to different columns of pixels. The wavelength corresponding to the pixel column at the incident position Pr becomes the Raman peak of the reference sample 26, and the wavelength corresponding to the pixel column at the incident position Ps becomes the Raman peak of the measurement sample 22. The processing device 50 performs fitting for the measured spectrum data and thereby determines the peak positions. As shown in FIG. 6B, the processing device 50 determines each of the peak positions and calculates a difference Δ1 between the peak positions.

Figure 6C:
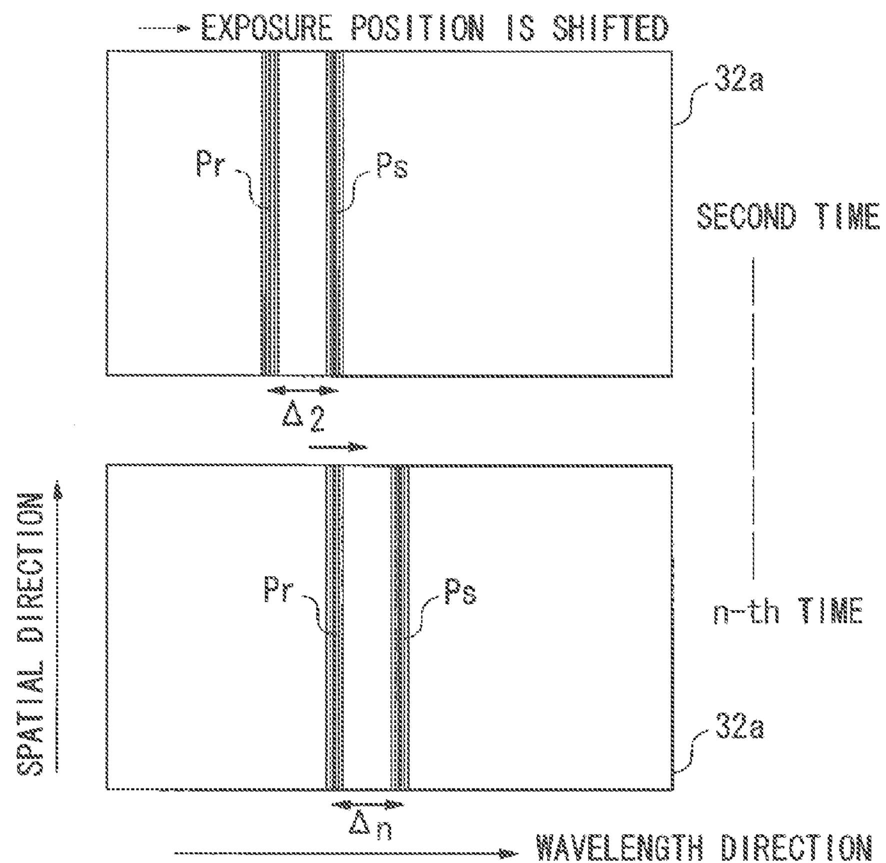
FIG. 6C is a figure for explaining a principle for measuring peak position in a spectrum.

Next, the measurement wavelength range of the spectroscope 31 is shifted by rotating the grating of the spectroscope 31 or by using a similar technique. That is, the wavelength range that is dispersed over a column of pixels of the detector 32 is changed by the spectroscope 31, and then spectrum measurement is carried out (FIG. 6C). In this way, a spectrum having a different wavelength range is measured. Note that the wavelength range is changed so that a Raman peak is included in the new wavelength range. Further, a difference between the peak position of the reference sample 26 and the peak position of the measurement sample 22 is measured in as similar manner. In this way, a difference Δ2 between the peak positions can be obtained. Further, the measurement wavelength is shifted and a difference between peak positions is obtained. By repeating these processes, it is possible to calculate differences Δ1 to Δn between peak positions (n is integer no less than two). By using the mean value of the peak position differences Δ1 to Δn, it is possible to reduce the effect caused by the sensitivity variations. Even when line illumination is performed, it is possible to align the exciting light intensity distribution and the detection sensitivity distribution with ease.

In this exemplary embodiment, since line illumination is performed by the Y-scan device 13, Raman scattered lights generated in the reference sample 25 and the measurement sample 22 enter a plurality of pixels of the detector 32 that are arranged along the entrance slit 30. The spectrums of the measurement sample 22 and the reference sample 26 are measured while the wavelength range that is dispersed over pixels of the detector 32 is changed by the spectroscope 31. Note that the line illumination is not limited to the cases where the scanning is performed at a higher speed than one frame of the detector as described above, but includes cases where a spot of laser light is converted into a line-like shape. That is, when Raman scattered light is detected by using a plurality of pixels of the detector 33 that are arranged along the entrance slit 30, the measurement is carried out while shifting the wavelength range by the spectroscope 31 as described above.

Figure 7:
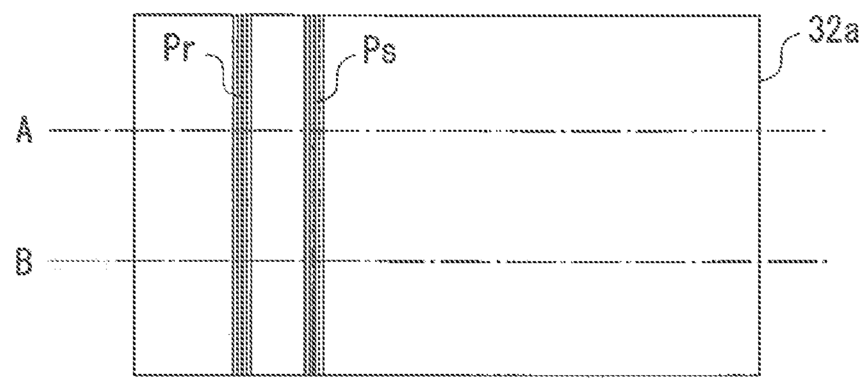
FIG. 7 is a figure for explaining a principle for measuring a peak position in a spectrum.
Figure 7:
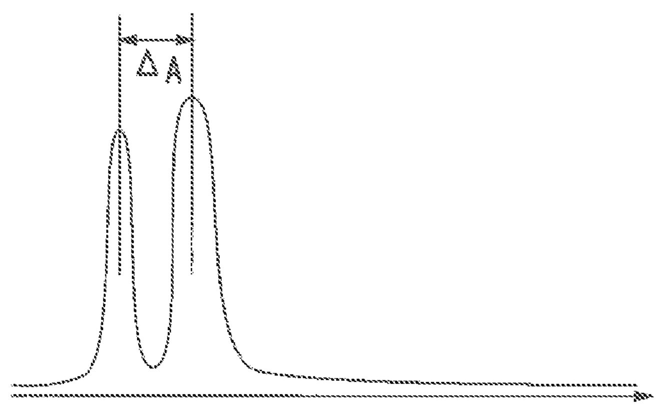
Figure 7:
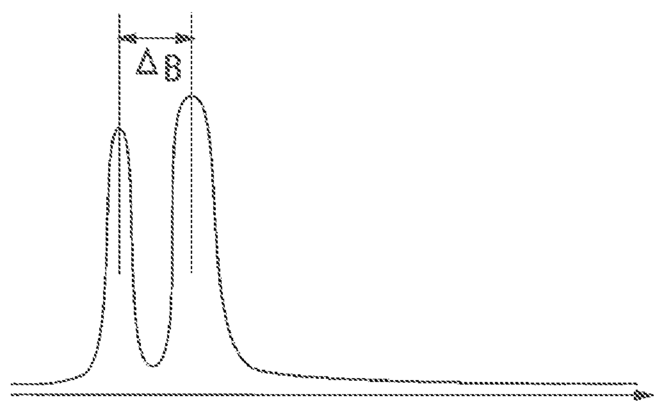

Further, in the case of line illumination and/or line detection, a Raman peak may be obtained in each of a plurality of pixels arranged along the line. For example, as shown in FIG. 7, rows of pixels corresponding to the wavelength are represented by a pixel row A and a pixel row B. Each of the peak positions of the reference sample 26 and the measurement sample 22 is obtained from a spectrum in the pixel row A. Then, a difference ΔA between the peak positions in the pixel row A is calculated. Similarly, each of the peak positions of the reference sample 26 and the measurement sample 22 is obtained from a spectrum in the pixel row B. Then, a difference ΔB between the peak positions in the pixel row B is calculated. By detecting a line-like area all at once in this manner, the distribution can be measured at high speed. That is, since peak positions can be detected at a plurality of points by using one frame of the detector 32, the measurement time can be reduced even when a stress distribution and/or a temperature distribution is measured. Note that although peak positions are detected at two points in the direction along the entrance slit in the above explanation, a peak position may be detected at each of three or more points. Further, a peak position may be calculated at each point based on the total value of as plurality of pixels.

By using the above-described spectrometry device, it is possible to measure a peak shift in a Rama spectrum. Further, it is possible to perform peak-shift imaging of a Raman spectrum. Further, it is possible to measure a temperature distribution and/or a stress distribution by scanning a measurement sample. Note that although the spectrometry device 100 that performs spectrometry for Raman scattered light is explained in above explanation, the present invention not limited to this spectrometry device. The present invention can be applied to any spectrometry device that detects outgoing light that is emitted from as sample and has a laser wavelength different from that of the incident light. For example, the present invention may be applied to a spectrometry device that detects fluorescence excited by exciting light and a spectrometry device that detects infrared absorption. Even in these spectrometry devices, a spectrum can be measured in a short time.

This application is based upon and claims the benefit of priority from Japanese patent application No. 2010-191946, filed on Aug. 30, 2010, the disclosure of which is incorporated herein in its entirety by reference.

INDUSTRIAL APPLICABILITY

The present invention can be used for spectrometry in which light from a sample is dispersed and measured.

REFERENCE SIGNS LIST

10 LASER LIGHT SOURCE
11 BEAM EXPANDER
13 Y-SCAN DEVICE
14 LENS
15 IRIS
16 LENS
17 BEAM SPLITTER
18 X-SCAN MIRROR
19 LENS
20 LENS
21 OBJECTIVE LENS
22 MEASUREMENT SAMPLE
23 STAGE
24 LENS
26 REFERENCE SAMPLE
30 ENTRANCE SLIT
31 SPECTROSCOPE
32 DETECTOR
40 STAGE DRIVE DEVICE
50 PROCESSING DEVICE
101 LASER LIGHT SOURCE
102 BEAM EXPANDER
103 BEAM SPLITTER
104 LENS
105 LENS
106 OBJECTIVE LENS
107 LENS
108 ENTRANCE SLIT
109 SPECTROSCOPE
110 DETECTOR
111 PROCESSING DEVICE
120 REFERENCE SAMPLE
121 MEASUREMENT SAMPLE

The invention claimed is:

1. A spectrometry device that performs spectrometry for light from a measurement sample and a reference sample and thereby detects respective peak positions in spectrums of the light from the measurement sample and the reference sample, comprising:
- a light source;
- a first lens that concentrates a light beam from the light source on the reference sample;
- a second lens that concentrates a light beam that has passed through the first lens on the measurement sample;
- a spectroscope that disperses light that is generated in the measurement sample and the reference sample by irradiation of the light beam and has a different wavelength from that of the light beam into a spectrum, wherein the spectroscope dispersing the light in a first direction;
- a detector that detects light that is dispersed by the spectroscope, wherein the detector is a 2D array detector including a plurality of pixels arrange in the first direction; and
- a light splitter for separating an optical path of light that is heading from the reference sample and the measurement sample toward the spectroscope from an optical path of a light beam that is heading from the light source toward the measurement sample, wherein
- a peak wavelength of a spectrum of light that is dispersed by the spectroscope is obtained, and a peak wavelength of light generated in the reference sample is compared with a peak wavelength of light generated in the measurement sample so that the peak wavelength is calibrated while taking account of a fluctuation of a wavelength of a light beam from the light source,
- wherein the reference sample is movably disposed along an optical axis of the first lens to focus the light beam from the first lens on the reference sample,
- wherein the detector detects the light generated in the measurement sample and the reference sample through a confocal optical system, and
- wherein an intensity of the light from the reference sample is adjusted by moving the reference sample in a direction in which the reference sample is deviated from a focal point of the first lens along an optical axis of the first lens.

2. The spectrometry device according to claim 1, further comprising a processing device that refers to known spectrum information of the reference sample and thereby distinguishes between a peak position in a spectrum of the light from the reference sample and a peak position in a spectrum of the light from the measurement sample.

3. The spectrometry device according to claim 1, wherein the reference sample is disposed on an optical axis of the first lens, and a light beam from the light source passes through the reference sample and then is incident on the measurement sample through the second lens.

4. The spectrometry device according to claim 1, wherein the reference sample is movably disposed so that a distance from the reference sample to the first lens can be changed.

5. The spectrometry device according to claim 1, wherein light that is heading from the reference sample and the measurement sample toward the spectroscope is incident on a plurality of pixels of the detector, arranged along an entrance slit disposed on an incident side of the spectroscope, and spectrums of the measurement sample and the reference sample are measured by changing a wavelength range that is dispersed over pixels of the detector by the spectroscope.

6. The spectrometry device according to claim 1, wherein light that is heading from the reference sample and the measurement sample toward the spectroscope is incident on a plurality of pixels of the detector, arranged along an entrance slit disposed on an incident side of the spectroscope, and a peak position in a spectrum is detected at each of at least two places along a direction of the entrance slit.

7. A spectrometry method for performing spectrometry for light generated in a measurement sample and a reference sample and thereby detecting respective peak positions in spectrums of the measurement sample and the reference sample, comprising:

a step of concentrating a light beam from a light source on the reference sample by a first lens;

a step of concentrating a light beam that has passed through the first lens on the measurement sample by a second lens;

a step of splitting light that is generated in the measurement sample and the reference sample by irradiation of the light beam and has a different wavelength from that of the light beam from light that is heading from the light source toward the measurement sample;

a step of dispersing light that is generated in the measurement sample and the reference sample and has a different wavelength from that of the light beam into a spectrum; and a step of obtaining a peak wavelength of a spectrum of light that is dispersed by the spectroscope, wherein the spectroscope disperses the light in a first direction, using a 2D array detector which includes a plurality of pixels arranged in the first direction, and comparing a peak wavelength of light generated in the reference sample with a peak wavelength of light generated in the measurement sample so that the peak wavelength is calibrated while taking account of a fluctuation of a wavelength of a light beam from the light source, wherein the reference sample is movably disposed along an optical axis of the first lens to focus the light beam from the first lens on the reference sample, wherein the light generated in the measurement sample and the reference sample is detected through a confocal optical system, and wherein an intensity of the light from the reference sample is adjusted by moving the reference sample in a direction in which the reference sample is deviated from a focal point of the first lens along an optical axis of the first lens.

8. A spectrometry device that performs spectrometry for light from a measurement sample and a reference sample and thereby detects respective peak positions in spectrums of the light from the measurement sample and the reference sample, comprising:

a light source;

a first lens that concentrates a light beam from the light source on the reference sample;

a second lens that concentrates a light beam that has passed through the first lens on the measurement sample;

a spectroscope that disperses light that is generated in the measurement sample and the reference sample by irradiation of the light beam and has a different wavelength from that of the light beam into a spectrum;

a detector that detects light that is dispersed by the spectroscope;

light splitter for separating an optical path of light that is heading from the reference sample and the measurement sample toward the spectroscope from an optical path of a light beam that is heading from the light source toward the measurement sample; and scanner for deflecting the light beam and thereby scanning a position of a light beam on the measurement sample, wherein the reference sample is disposed out of an optical axis of the first lens, and the scanner deflects the light beam and thereby makes the light beam that is originally incident on the measurement sample incident on the reference sample.

9. A spectrometry method for performing spectrometry for light generated in a measurement sample and a reference sample and thereby detecting respective peak positions in spectrums of the measurement sample and the reference sample, comprising:

a step of concentrating a light beam from a light source on the reference sample by a first lens;

a step of concentrating a light beam that has passed through the first lens on the measurement sample by a second lens;

a step of splitting light that is generated in the measurement sample and the reference sample by irradiation of the light beam and has a different wavelength from that of the light beam from light that is heading from the light source toward the measurement sample;

a step of dispersing light that is generated in the measurement sample and the reference sample and has a different wavelength from that of the light beam into a spectrum; and a step of deflecting the light beam and thereby scanning a position of a light beam on the measurement sample, wherein the reference sample is disposed out of an optical axis of the first lens, and a scanner deflects the light beam and thereby makes a light beam that originally is incident on the measurement sample incident on the reference sample.

10. The spectrometry method according to claim 9, wherein a peak position in a spectrum of light from the reference sample and a peak position in a spectrum of light from the measurement sample are distinguished by referring to known spectrum information of the reference sample.

11. The spectrometry method according to claim 9, wherein the reference sample is disposed on an optical axis of the first lens, and a light beam from the light source passes through the reference sample and then is incident on the measurement sample through the second lens.

12. The spectrometry method according to claim 9, wherein the reference sample is movably disposed so that a distance from the reference sample to the first lens can be changed.

13. The spectrometry method according to claim 9, wherein a light beam from the light source is concentrated into a line-like spot and then is incident on the measurement sample and the reference sample, and spectrums of the measurement sample and the reference sample are measured by changing a wavelength range that is dispersed over pixels of the detector by the spectroscope.

14. The spectrometry method according to claim 9, wherein a peak position of the light from the measurement sample is measured by using at least two peak positions contained in known spectrum information of the reference sample.

15. The spectrometry method according claim 9, wherein light that is heading from the reference sample and the measurement sample toward the spectroscope is incident on a plurality of pixels of the detector, arranged along an entrance slit disposed on an incident side of the spectroscope, and a peak position in a spectrum is detected at each of at least two places along a direction of the entrance slit.

* * * * *